United States Patent [19]

Lee

[11] 4,299,780
[45] Nov. 10, 1981

[54] PROCESS FOR PREPARING SALTS OF CARBAMOYL SULFONIC ACID DERIVATIVES

[75] Inventor: Young-Jin Lee, South Charleston, W. Va.

[73] Assignee: Union Carbide Corporation, New York, N.Y.

[21] Appl. No.: 133,790

[22] Filed: Mar. 25, 1980

[51] Int. Cl.$^3$ .................. C07C 143/02; C07C 143/52; A01N 47/10
[52] U.S. Cl. ........................... 260/513 N; 260/507 R; 424/300
[58] Field of Search ........................ 260/545 R, 513 N

[56] References Cited

U.S. PATENT DOCUMENTS 2,906,776  9/1959  Doser .................................. 260/534

OTHER PUBLICATIONS

Guise et al., "The Reaction of Isocyanates with Bisulphite", *Aust. J. Chem.*, 1972, 25, 2583-2595.

*Primary Examiner*—Alan Siegel
*Attorney, Agent, or Firm*—Dale Lynn Carlson; Gerald Lynn Coon

[57] ABSTRACT

This invention relates to a process of preparing a compound of the formula:

$$R-NHCOSO_3^- M^+$$

wherein R is a $C_1$—$C_8$ alkyl or phenyl group and M is an alkali metal or ammonium ion.
Also encompassed by the present invention is a novel class of compounds, namely salts of N-methylcarbamoylsulfonic acids.

6 Claims, No Drawings

PROCESS FOR PREPARING SALTS OF CARBAMOYL SULFONIC ACID DERIVATIVES

FIELD OF THE INVENTION

This invention relates generally to the preparation of salts of carbamoyl sulfonic acid derivatives and, more particularly to a method of preparing these compounds.

BACKGROUND OF THE INVENTION

Certain carbamoyl sulfonic acid derivatives are well-known in the art. These derivaties are typically prepared by reacting sodium bisulfite with an isocyanate to form the desired derivative. By way of illustration, on article by G. B. Guise, M. B. Jackson and J. A. Maclaren entitled "The Reaction of Isocyanates with Bisulphite Salts" appearing in *Aust. J. Chem.*, 1972, 25, 2583-95, describes the reaction of n-butylisocyanate with bisulphite to form the salt of n-butylcarbamoyl sulfonic acid. As a further example, U.S. Pat. 2,906,776 discloses carbamic acid impregnating agents for treating textiles, wherein the agents are prepared by reacting an alkali metal bisulfite with a higher aliphatic isocyanate.

The above prior art method of preparing carbamoyl sulfonic acid derivatives leaves something to be desired, however, since the reactive nature of the isocyanates, particularly with water, often necessitates special precautions in their transportation and storage and handling. Consequently, there exists a need for a process of preparing these derivatives that does not employ an isocyanate reactant.

OBJECTS

It is an object of the present invention to provide a process for preparing salts of carbamoyl sulfonic acid derivatives that does not employ an isocyanate reactant or any other reactant that requires special precautions in transportation and storage or handling.

It is another object of the present invention to provide a novel compound that is useful as an intermediate in the preparation of N-methyl carbamate compounds which are known to exhibit outstanding insecticidal activity.

These and other objects will become apparent from a reading of the following detailed specification.

SUMMARY OF THE INVENTION

According to the present invention, there is provided an improved method for preparing a compound of the formula:

R-NHCOSO$_3$<sup>-</sup> M<sup>+</sup> which comprises reacting a compound of the formula:

with a compound of the formula:

R-NHCOX, in the presence of a base,
wherein
R is a substituted or unsubstituted C$_1$-C$_8$ alkyl or phenyl group,
M<sup>+</sup> is an alkali metal or ammoniumion, and
X is halogen (preferably chlorine).

Also encompassed by the present invention is a novel class of compounds, alkali metal and ammonium salts of N-methylcarbamoylsulfonic acid having the formula:

wherein M<sup>+</sup> is defined above.

The compounds produced in accordance with the process of the present invention are useful as intermediates in the production of N-alkyl carbamate compounds, known to possess outstanding insecticidal activity (aldicarb, carbaryl and methomyl and the like), produced by the method of co-pending U.S. application Ser. No. (12,210) by the inventor herein.

DESCRIPTION OF THE PREFERRED EMBODIMENTS

The molar amount of reactants can vary over a wide range. For example, the molar ratio of phenyl-or alkyl-carbamoyl halide to bisulfite reactant can vary from 9:1 or higher to 1:9 or lower, although the preferred ratio is 1:1 or 1:2 if busulfite is used as a base as well as a reactant. The bisulfite reactant can be ammonium or any alkali metal bisulfate such as, for example, sodium, potassium, lithium, and the like.

The reaction in accordance with the process of the present invention may be conducted in the presence of a solvent. The preferred solvent is water, or water together with an organic solvent that is inert to the reactants. Example of useful organic co-solvents include toluene, methylene chloride and chloroform. The amount of solvent is not critical and is known to those of ordinary skill in the art.

The reaction temperature can vary over a wide range and is not narrowly critical. The preferred reaction temperature is between about 0° C. and about 50° C., although higher temperatures up to the boiling point of any solvent used, and not exceeding the degradation temperature of the reactants, can be employed. The more preferred temperature is room temperature.

The process of the present invention can be effected at atmospheric or superatmospheric pressure. If an open reactor is used, atmospheric pressure is preferred. If an enclosed reactor is used, autogenous pressure is preferred. The process can be conducted in batch, semi-continuous or continuous fashion.

The reaction time is not critical and can vary from a few minutes to a day or more, depending upon the reaction conditions (temperature, pressure, etc). The reaction time is preferably several hours.

If purification of the product produced in accordance with the process of the present invention is desired, it can be made by conventional means such as re-crystallization in solvent.

The following example is intended to illustrate, but in no way limit, the present invention.

EXAMPLE I

To 10.4 g (0.1 mole) of sodium bisulfite in 20 ml of water was added 16.8 g of 28% solution of N-methyl-carbamoyl chloride (0.05 mole ) in methylene chloride over a 4 minute period. Stirring of the reaction mixture was contained for 2 hrs. at 20° C. The methylene chloride and water were removed under reduced pressure resulting in 8.1 g of white solid product. Nuclear magnetic resonance (NMR) testing showed the presence of sodium N-methylcarbamoylsulfonate, together with some unidentified impurities.

COMPARISON A

To a solution of 52 g (0.5 mole) of sodium bisulfite in 100 ml of water was added 28 g (0.5 mole) of methylisocyanate over a one hour period with vigorous stirring at 20°–26° C. The resulting solution was further stirred for 2 hr at room temperature and then the water was evaporated under reduced pressure at 25°–30° C. The product was vacuum dried overnight at 35° C. to give 80.6 g (100%) of the white solid product, identified by NMR to be sodium N-methylcarbamoylsulfonate.

What is claimed is:

1. A process for preparing a compound of the formula:

$$R\text{-NHCOSO}_3^- M^+$$

which comprises reacting a compound of the formula:

$$M^+ HSO_3^-$$

with a compound of the formula $$R\text{-NHCOX}$$

wherein
R is a $C_1$ to $C_8$ alkyl or phenyl group,
$M^{30}$ is an alkali metal or ammonium ion, and
X is halogen,
said reaction being effected at a temperature between about 0° C. and about 50° C. and at a pressure of autogenous or atmospheric pressure.

2. The process of claim 1 wherein said reaction is conducted in the presence of a solvent.

3. The process of claim of claim 2 wherein the solvent is water.

4. The process of claim 2 wherein the solvent is a mixture of water and an organic co-solvent.

5. The process of claim 1 wherein N-methylcarbamoyl chloride is reacted with sodium bisulfite to prepare the sodium salt of N-methylcarbamoylsulfonic acid.

6. A compound of the formula:

$$CH_3\text{-NHCOSO}_3^- M^+$$

wherein M is alkali metal or ammonium.

* * * * *